(12) United States Patent
Kim et al.

(10) Patent No.: US 8,409,608 B2
(45) Date of Patent: Apr. 2, 2013

(54) METHODS FOR PRODUCING SILVER-BONDED ANTIMICROBIAL MOIST WOUND DRESSINGS AND MOIST WOUND DRESSINGS PRODUCED BY THE METHODS

(75) Inventors: Yoong-Soo Kim, Seoul (KR); Ju-Young Kim, Seoul (KR)

(73) Assignee: Cellulose Concepts, LLC, Tallahassee, FL (US)

(*) Notice: Subject to any disclaimer, the term of this patent is extended or adjusted under 35 U.S.C. 154(b) by 0 days.

(21) Appl. No.: 13/607,401

(22) Filed: Sep. 7, 2012

(65) Prior Publication Data

US 2013/0006161 A1    Jan. 3, 2013

Related U.S. Application Data

(62) Division of application No. 12/282,344, filed as application No. PCT/KR2007/001173 on Mar. 9, 2007, now Pat. No. 8,263,116.

(30) Foreign Application Priority Data

Mar. 10, 2006  (KR) .................. 10-2006-0022818

(51) Int. Cl.
*A61F 13/02* (2006.01)
*A61L 15/00* (2006.01)
*A61K 33/38* (2006.01)

(52) U.S. Cl. ........... 424/448; 424/447; 424/618; 602/48

(58) Field of Classification Search .................. None
See application file for complete search history.

(56) References Cited

U.S. PATENT DOCUMENTS

| | | |
|---|---|---|
| 4,977,892 A | 12/1990 | Ewall |
| 5,147,339 A | 9/1992 | Sundstrom |
| 5,681,579 A | 10/1997 | Freeman |
| 5,709,870 A | 1/1998 | Yoshimura et al. |
| 5,941,840 A | 8/1999 | Court et al. |
| 6,087,549 A | 7/2000 | Flick |
| 6,379,712 B1 | 4/2002 | Yan et al. |
| 6,719,987 B2 | 4/2004 | Burrell et al. |
| 6,897,349 B2 | 5/2005 | Gibbins et al. |
| 2002/0073891 A1 | 6/2002 | Parsons et al. |
| 2006/0149182 A1 | 7/2006 | Cullen et al. |

FOREIGN PATENT DOCUMENTS

| | | |
|---|---|---|
| CN | 1129518 A | 8/1996 |
| EP | 707793 A1 | 4/1996 |
| JP | 2-501199 A | 4/1990 |
| JP | 3-242145 A | 10/1991 |
| JP | 7-444 A | 1/1995 |
| JP | 8-113507 A | 5/1996 |
| JP | 2004508895 A | 3/2004 |
| JP | 2004520096 A | 7/2004 |
| JP | 2005501982 A | 1/2005 |
| JP | 2005510296 A | 4/2005 |
| KR | 2003-0070038 | 8/2003 |
| KR | 2004-0051130 | 6/2004 |
| WO | WO-8902754 A1 | 4/1989 |
| WO | WO-0224240 A1 | 3/2002 |
| WO | WO-0238097 A1 | 5/2002 |
| WO | WO-02/43743 A1 | 6/2002 |
| WO | WO-03022317 A1 | 3/2003 |
| WO | WO-03045294 A1 | 6/2003 |
| WO | WO-2004/024197 A1 | 3/2004 |
| WO | WO-2005/075164 A2 | 8/2005 |

OTHER PUBLICATIONS

Rowe et al., "Carboxymethylcellulose Sodium", The Handbook of Pharmaceutical Excipients, 2003, pp. 97-100, 4th Edition.

Ju et al., "Research on the process for base-treated cotton yarns carrying silver and the antibioticity" Textile Auxiliaries, Dec. 2005, vol. 22, No. 12.

*Primary Examiner* — Robert A Wax
*Assistant Examiner* — Sarah Park
(74) *Attorney, Agent, or Firm* — McDermott Will & Emery LLP

(57) ABSTRACT

Methods for producing silver-bonded antimicrobial moist wound dressings include adding a silver-containing compound to a 0.1-30% aqueous solution of an alkaline solvent to dissociate silver ions from the silver-containing compound; dissolving CMC in water or an organic solvent to obtain a CMC solution; mixing the silver ion-containing solution with the CMC solution so that the hydrogen ions ($H^+$) of the hydroxyl groups of the CMC are replaced by the silver ions to prepare a silver-CMC compound; dispersing and absorbing the silver-CMC compound in a medium; and drying the medium.

11 Claims, 3 Drawing Sheets

(a)

(b)

METHODS FOR PRODUCING SILVER-BONDED ANTIMICROBIAL MOIST WOUND DRESSINGS AND MOIST WOUND DRESSINGS PRODUCED BY THE METHODS

CROSS-REFERENCE TO RELATED APPLICATIONS

This application is a divisional of U.S. patent application Ser. No. 12/282,344, filed Sep. 9, 2008, which is a 35 U.S.C. §371 National Stage Entry of International Patent Application PCT/KR2007/001173, filed Mar. 9, 2007, which claims the priority of Korean Patent Application 10-2006-0022818, filed Mar. 10, 2006, each of which is incorporated herein by reference in its entirety.

TECHNICAL FIELD

The present invention relates to methods for producing antimicrobial moist wound dressings with antimicrobial activity in which sodium carboxymethyl cellulose ($C_6H_9OCH_2COONa$, hereinafter abbreviated as CMC) is chemically bonded to silver. More specifically, the present invention relates to silver-bonded antimicrobial moist wound dressings that can be used to treat and prevent infection caused by various species of pathogenic bacteria using a silver-CMC compound, which is prepared by replacing the hydrogen ions ($H^+$) of the hydroxyl groups of CMC with silver ions ($Ag^+$) (i.e. by alkoxylation).

BACKGROUND ART

Moist wound dressings are products that cover wounds and keep the wounds in a moist environment. Moist wound dressings have been developed for recent 20 or more years at a greater speed than they had been developed over the previous hundred or more years. Many clinical results on moist wound dressings have revealed the stability and efficiency of a moist environment provided by the moist wound dressings in the treatment of chronic wounds, which have been considered as being impossible to treat, as well as acute wounds.

Epithelial cells are regenerated without any particular difficulty along the surface of wounds in a moist environment. In contrast, epithelial cells are not regenerated along the surface of wounds in a dry environment, and instead, form routes under the skin, which is a moist environment, and are regenerated along the routes. Accordingly, regeneration of epithelial cells in a dry environment is retarded, and thus the wound healing becomes inefficient. In a dry environment, substances involved in wound healing, such as polymorphonuclear leukocytes, macrophages, proteases and cell growth factors, contained in wound exudate are released to the outside or dried, thus impeding their inherent functions. In contrast, a moist environment allows the substances to successfully perform their functions, leading to efficient wound healing.

Silver has been empirically recognized over the past several centuries for its excellent antimicrobial activity and sterilizing power in comparison with other heavy metals. With the advance of modern sciences since the early twentieth century, the antimicrobial activity of silver and its mechanisms have been scientifically verified through systematic research conducted by many scientists.

Since the discovery of the first antibiotic, penicillin, bacteria resistant to penicillin have been reported. Many research results reveal that an extremely small amount of silver shows sufficiently effective antimicrobial activity against bacteria, such as the so-called superbacteria, resistant to methicillin and vancomycin, which is known as most effective antibiotic among those hitherto developed after penicillin, and possess broad spectrum antimicrobial effects against bacteria, including gram-positive and gram-negative bacteria, fungi and yeasts. Particularly, based on the fact that no silver-resistant bacteria have hitherto been reported, it is known that silver has less problems of resistance than other antimicrobial agents.

Such advantages of silver have been most successfully utilized in medical products. Development of nanotechnology since the early twenty-first century has provided a background for the efficient use of expensive silver from both technical and economic viewpoints. Taking advantage of the public's interest in the so-called well-being syndrome, development of products based on silver nanotechnology has been booming. Of these products, representative medical-related products are antimicrobial wound dressings for the treatment of acute wounds, e.g., burns, and chronic wounds, e.g., decubitus ulcers and diabetic foot ulcers.

Since serious burns of second-degree or higher and chronic wounds destroy the body protection functions of skin, bacterial infection of the wound sites occurs and/or a large amount of wound exudate is continuously secreted from the wound sites. Such bacterial infection makes the depth of the wound deeper. As the average human life has recently increased, the number of old patients with various kinds of chronic wounds has been rapidly increased.

Representative therapeutic methods for treating chronic wounds are associated with the use of antimicrobial agents for external application to treat and prevent bacterial infection and the use of wound dressings capable of absorbing wound exudate. Thus, there is an urgent need for an economically advantageous antimicrobial moist wound dressing that provides sufficient antimicrobial activity and is capable of effectively absorbing wound exudate.

Commercially available wound dressings using silver can be categorized into the following products.

The first products are dry wound dressings in which finely divided silver nanoparticles, e.g., nanocrystalline silver, prepared by nanotechnology are electrically coated on a polyurethane mesh fiber having a monolayer structure, and their similar products (U.S. Pat. Nos. 6,719,987 and 6,087,549). Since these products contain an excessively large amount of silver, they show superior antimicrobial activity, but are highly cytotoxic to normal cells. In addition, another disadvantage of the products is that the silver tends to fall off from the products, leading to temporary discoloration of applied skin sites. Furthermore, the products need wetting with distilled water before use, causing inconvenience in use. Moreover, since the products have a low exudate absorption capacity, they do not provide a sufficient moist environment.

The second products are wound dressings in which nanometer-sized silver precipitated by a chemical reaction is physically diffused or dispersed between fiber tissues, and their similar products (U.S. Pat. No. 6,897,349). These products provide a moist environment due to their high absorption capacity, but do not exert sufficient antimicrobial activity because of their low silver content. As a result, the products disadvantageously fail to achieve desired therapeutic effects.

Cream or gel type products (e.g., Flamazine) containing 1% of highly toxic silver nitrate, are also known. Although these products show superior antimicrobial activity as antimicrobial agents for external application, they are highly cytotoxic due to their high silver content and have no absorption capacity in view of their intrinsic characteristics.

The aforementioned products developed based on silver nanotechnologies have some problems in their structures in that the size and shape of nanoparticles are non-uniform, the distribution of particles is not readily controlled, control of the silver concentration and content is difficult, and high production costs are required. In addition, since silver is not chemically bonded but physically attached to the products, the finely divided silver nanoparticles become likely to fall off from the products. The fallen silver particles show high toxicity to not only various species of harmful bacteria but also normal human cells, thus causing serious health problems in humans.

Some research results show that the use of an extremely low concentration of silver for the treatment of burns results in about a five-fold increase in the metabolism rate of cells. If the silver is used in an amount exceeding the antimicrobial activity sufficient to treat infection, high cytotoxicity to normal cells is caused, thus posing a health hazard to humans. Consequently, in the case where products highly susceptible to falling of finely divided silver particles, which are developed based on silver nanotechnology, are directly used on the surface of wounds whose body protection functions are destroyed, the silver particles may be accumulated on respective human organs or easily penetrated into cells, thus being toxic to the cells. In this case, there exists a risk of causing life-threatening results.

There have been a series of research reports on the so-called Nano-ecology concerning the possibility that nanoparticles may adversely affect human health. Further, the safety of nanotechnology has been continuously questioned. Under these circumstances, the use of wound dressings produced by silver nanotechnology should be seriously reconsidered in view of potential dangers of the products. Moreover, excessive use of silver is economically disadvantageous and is environmentally unfriendly.

On the other hand, enclosed-type moist dressings employ hydrophilic polymers, such as hydrocolloids, hydrogels, polyurethane and calcium alginate, to absorb wound exudate so that a moist environment is provided and thus superior therapeutic effects are achieved. However, since these products contain no pharmacologically effective ingredient, they cannot be used on infected wound sites. In addition, the products cannot be combined with antimicrobial agents for external application, which impedes the growth of skin regenerative cells. Furthermore, the products have a disadvantage in use that bacteria must be previously removed from infected wounds.

More seriously, moist environment provides an optimal environment in which bacteria can proliferate and grow. Although there is little possibility of bacterial infection in clean wound sites, people having limited medical knowledge on wound infection are exposed to unexpected additional risks, such as aggravation of wound sites resulting from infection and increased treatment period and costs. Therefore, there is a demand to improve the limited functions, such as prevention of secondary infection from the environment, protection of wounds and provision of a moist environment, of currently available enclosed-type moist wound dressings by imparting antimicrobial activity to the wound dressings.

DISCLOSURE OF INVENTION

Technical Problem

Therefore, it is an object of the present invention to provide medically safe antimicrobial moist wound dressings that have minimum toxicity to the growth of normal cells while exhibiting sufficient antimicrobial activity against various species of pathogenic bacteria, absorb wound exudate to provide a moist environment without sticking to the surface of wounds, and generate no falling of silver, thereby preventing penetration of the silver into the body.

Technical Solution

In accordance with one aspect of the present invention for achieving the above object, there is provided a method for producing a silver-bonded antimicrobial moist wound dressing, comprising the steps of: adding a silver-containing compound to a 0.1-30% aqueous solution of an alkaline solvent to dissociate silver ions from the silver-containing compound; dissolving CMC in water or an organic solvent to obtain a CMC solution; mixing the silver ion-containing solution obtained in the first step with the CMC solution obtained in the second step so that the hydrogen ions ($H^+$) of the hydroxyl groups of the CMC are replaced by the silver ions to prepare a silver-CMC compound; dispersing and absorbing the silver-CMC compound in a medium; and drying the medium.

In accordance with another aspect of the present invention, there is provided an antimicrobial moist wound dressing comprising a layer in which a silver-CMC compound is dispersed in a medium (hereinafter, also referred to simply a medium layer), a pressure-sensitive adhesive layer and an external protective film layer laminated and joined to each other, wherein the silver-CMC compound is prepared by replacing the hydrogen ions of the hydroxyl groups ($OH^-$) of CMC with silver ions.

In accordance with yet another aspect of the present invention, there is provided an antimicrobial moist wound dressing comprising a pressure-sensitive adhesive layer in contact with skin, a silver-CMC powder-containing layer and an external protective film layer laminated and joined to each other, wherein the silver-CMC powder is prepared by drying a compound in which the hydrogen ions of the hydroxyl groups ($OH^-$) of CMC are replaced by silver ions, followed by pulverization.

The antimicrobial moist wound dressings of the present invention exhibit antimicrobial activity sufficient to effectively treat or prevent serious infection, which is a cause of aggravation of wound sites, retardation of treatment and incidence of complications, caused by various species of pathogenic bacteria, and absorb wound exudate to provide a moist environment where the growth rate of epithelial cells for skin regeneration is rapidly increased and superior therapeutic effects, e.g., alleviation of pains, shortening of treatment period and minimization of cicatrices after treatment, can be achieved. In addition, since the antimicrobial moist wound dressings of the present invention do not readily stick to the surface of wounds, they can minimize pains without any additional trauma during exchange of the wound dressings. Particularly, the method of the present invention enables the production of enclosed-type antimicrobial moist dressings capable of overcoming the greatest problem, i.e. provision of optimum conditions for bacterial proliferation, of conventional moist dressings, and creating a good therapeutic environment.

BRIEF DESCRIPTION OF THE DRAWINGS

The above and other objects, features and other advantages of the present invention will be more clearly understood from the following detailed description taken in conjunction with the accompanying drawings, in which.

BEST MODE FOR CARRYING OUT THE INVENTION

Figure 1:
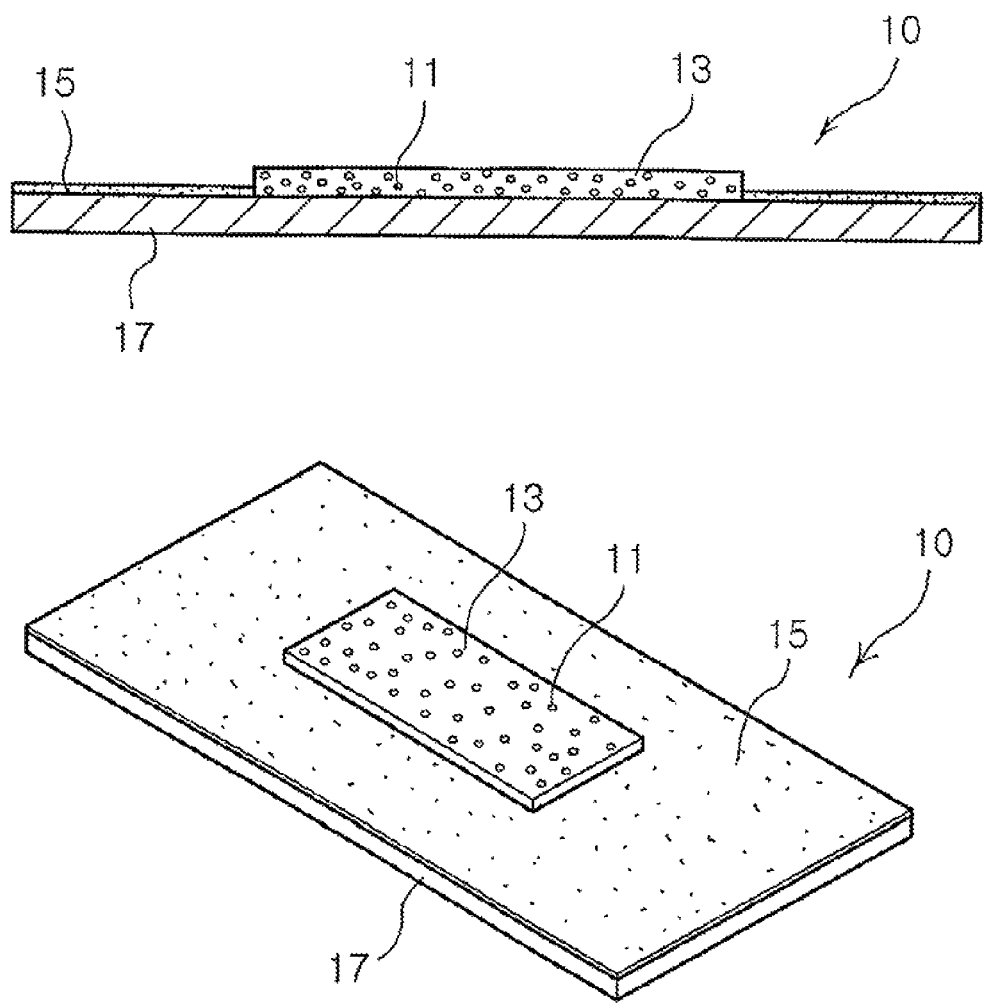
FIG. 1 schematically shows an antimicrobial moist wound dressing comprising a layer in which a silver-CMC compound is dispersed in a medium, according to one embodiment of the present invention.

The present invention will be described in greater hereinbelow.

In the first step of the method according to the present invention, a silver-containing compound is added to a 0.1-30% aqueous solution of an alkaline solvent to dissociate silver ions from the silver-containing compound. As a result, a silver ion-containing solution can be obtained.

As the silver-containing compound, there can be used a silver halide, e.g., silver bromide, silver iodide, silver fluoride or silver chloride, silver acetate, silver carbonate, silver fulminate, silver nitrate, silver oxide, silver perchlorate, silver phosphate, silver sulfate, silver triocyanate, or the like. Preferably, a silver halide, particularly silver chloride (AgCl), can be used.

The amount of the silver-containing compound added to the aqueous solution is in the range of 0.00001% to 20.0% (w/v). When the amount of the silver-containing compound added is less than 0.00001% (w/v), sufficient antimicrobial activity cannot be expected. Meanwhile, when the amount of the silver-containing compound added to the aqueous solution exceeds 20.0% (w/v), the silver particles still remain, causing damage to humans. The silver-containing compound is preferably added in an amount of 0.1-6.0% (w/v).

Examples of suitable alkaline solvents include NaOH, $Ca(OH)_2$, $NH_4OH$, $Na_2S_2O_3$, $(NH_4)_2CO_3$, $NH_4Cl$, and KCN. $NH_4OH$ is preferably used. The concentration of the alkaline solvent in the aqueous solution is preferably in the range of 0.1% to 30.0%. When the concentration of the alkaline solvent is less than 0.1%, recrystallization of the silver cannot be prevented. Meanwhile, when the concentration of the alkaline solvent is more than 30%, the silver ions are no longer dissociated from the silver-containing compound, which is economically disadvantageous.

The alkaline solvent serves to dissociate silver ions ($Ag^+$) from the silver-containing compound and to prevent the recrystallization of the dissociated silver ions, rendering the silver-containing solution more homogeneous. Particularly, the alkaline solvent functions to replace the hydrogen ions ($H^+$) of the hydroxyl groups of CMC with the silver ions, as will be described below.

The time required for the dissociation is from 5 minutes to 24 hours. When the dissociation proceeds for less than 5 minutes, the silver-containing compound is not sufficiently dissociated into silver ions and undesirably remains in the form of particles. Meanwhile, when the dissociation proceeds for more than 24 hours, the silver-containing compound is sufficiently dissociated and thus no further dissociation occurs. Accordingly, the dissociation time is limited to the range defined above.

In the second step of the method according to the present invention, solid CMC is dissolved in water or an organic solvent to obtain a CMC solution. As the organic solvent, there may be exemplified ethanol or isopropyl alcohol. Ethanol is particularly preferred because it leaves no residue and is harmless to humans.

The mixing ratio between the CMC and the water or organic solvent can be varied depending on the stoichiometric ratio in which the CMC can be dissolved in the water or organic solvent. In addition, the mixing ratio can be suitably selected by those skilled in the art to which the present invention pertains. For example, the CMC can be mixed in an amount of 20-150 g with respect to 1,000 ml of the organic solvent, but the present invention is not limited to this mixing ratio.

In the third step of the method according to the present invention, the silver ion-containing solution is mixed with the CMC solution so that the hydrogen ions ($H^+$) of the hydroxyl groups of the CMC are replaced by the silver ions to prepare a silver-CMC compound.

In this step, the dissociated silver ions are chemically bonded to the CMC. Accordingly, the two solutions are mixed in such an amount that the silver ions can be sufficiently chemically bonded to the CMC. More specifically, it is preferred to mix the CMC in an amount of 5-35 g relative to 1,000 ml of the silver ion-containing solution.

The silver-CMC compound is prepared by mixing the CMC solution with the silver ion-containing solution. The chemical bonding between the silver ions and the CMC prevents dissolution of the silver ions from the silver-CMC compound. Accordingly, when the wound dressings of the present invention are attached to wound sites, no silver ions are dissolved from the wound dressings and thus damage to normal cells can be prevented, unlike in conventional wound dressings.

The reaction time required for the bonding of the silver ions with the CMC by mixing the CMC solution with the silver-ion containing solution is preferably from 1 second to 24 hours and more preferably from 10 seconds to 1 hour, but the present invention is not particularly limited to these ranges. The reaction time can be suitably selected within the ranges defined above.

By mixing the two solutions and maintaining the mixture for the given reaction time, the hydrogen ions of the hydroxyl groups of the CMC are replaced by the silver ions. The temperature for the replacement is desirably in the range of 20° C. to 50° C.

A process for making a silver-impregnated cellulose comprises associating silver ion ($Ag^+$) with CMC (Sodium Carboxymethyl Cellulose: $C_6H_9OCH_2COONa$), introducing the $Ag^+$-CMC complex into the cellulose matrix, and irreversibly associating the $Ag^+$-CMC complex with the cellulose matrix by drying the cellulose matrix, such that leaching will not occur upon rehydration. In the case where the hydrogen ions of the hydroxyl groups of the CMC are replaced by the silver ions, the silver ions are bonded in the form of AgO or silver oxide ($AgO_2^+$) to the hydroxyl groups, as depicted in Formula I below.

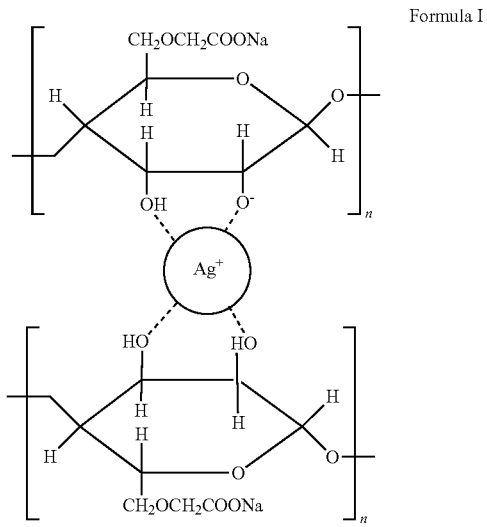

Formula I

Silver ion can have up to four ligands and it is well known that hydroxyl groups from C-2 and C-3 can bind to metal ions in a bidentate fashion. The C-3 hydroxyl group has the highest acidity among the three hydroxyl groups, so it is reasonable to believe that one of the C-3 hydroxyl groups binds to the silver in alkoxylate form. These hydroxyl groups effectively chelate to the metal ion and prevent its possible leaching in aqueous solution.

In the fourth step of the method according to the present invention, the silver-CMC compound is dispersed and absorbed in a medium. The medium must be able to disperse and absorb the silver-CMC compound, and may be an absorbable material capable of effectively absorbing both exudate secreted from wounds and the silver-CMC compound. As the medium, there can be used a pure (100%) cotton non-woven fabric or gauze.

The dispersion of the silver-CMC compound in the medium can be performed by dipping the medium in the silver-CMC compound, pouring the silver-CMC compound into the medium, or spraying the silver-CMC compound on the medium, and is not particularly limited to these dispersion processes.

In the fifth step of the method according to the present invention, the medium, in which the silver-CMC compound is dispersed, is dried at room temperature or using a dryer. It is preferred to perform the drying of the medium in a drying oven or using hot air. The drying of the medium can be performed without any particular limitation by any method known commonly in the art.

The drying conditions are not specially restricted. For example, in the case where the medium is pure (100%) cotton, the drying is preferably performed at 200° C. or lower. When the medium is dried above 200° C., the physical properties of the cotton are deteriorated and thus intended effects cannot be attained.

Since CMC can absorb and store moisture of ten or more times of its weight, the antimicrobial moist wound dressings produced by the method of the present invention provide and maintain a moist environment effective for the treatment of wounds when being attached to the wounds. In addition, since silver is bonded to CMC, the wound dressings of the present invention provide bactericidal and antimicrobial effects on wounds. Therefore, the wound dressings of the present invention eliminate the need for additional sterilization and disinfection of wounds except for contaminated wound sites.

According to another method of the present invention, the dried silver-CMC compound may be pulverized to form a hydrogel or hydropolymer, which is used to produce an enclosed-type antimicrobial moist wound dressing.

Next, the antimicrobial moist wound dressings of the present invention will be explained in more detail with respect to the accompanying drawings. The drawings may be exaggerated to assist the understanding of the present invention, but are not meant in any way to restrict the scope of the present invention.

The same elements are denoted by the same reference numerals even though they are depicted in different drawings, and description thereof is omitted.

FIG. 1 schematically shows an antimicrobial moist wound dressing 10 according to one embodiment of the present invention. Reference numeral 11 indicates a silver-CMC compound dispersed in a medium of the antimicrobial moist wound dressing 10, reference numeral 13 indicates a medium layer, reference numeral 15 indicates a pressure-sensitive adhesive layer, and reference numeral 17 indicates an external protective film layer. In FIG. 1, the silver-CMC compound 11 dispersed in a medium is exaggerated for the purpose of clarity.

As shown in FIG. 1, the antimicrobial moist wound dressing 10 of the present invention comprises the medium layer 13 in which the silver-CMC compound 11 is dispersed in a medium, the pressure-sensitive adhesive layer 15 and the external protective film layer 17 laminated and joined to each other.

The term joined as used herein means that the respective layers constituting the wound dressing 10 of the present invention are bonded to each other by means of an adhesive, or by thermal pressurization, or sonication. Alternatively, the term means that a solution constituting one layer of the layers is coated on other constituent layers so that all layers are attached and bonded to each other, and is meant to include simple laminates.

The silver-CMC compound 11 dispersed in the medium of the medium layer 13 is a compound in which the hydrogen ions of the hydroxyl groups ($OH^-$) of CMC are replaced by silver ions.

As the medium in which the silver-CMC compound 11 is dispersed, there can be used a pure (100%) cotton non-woven fabric or gauze. The silver-bonded CMC can absorb moisture of ten or more times of its weight. Therefore, since the moist wound dressing 10 of the present invention has high moisture absorption and storage capacity, it provides a moist environment effective for wound healing due to the silver-CMC compound 11 and inhibits proliferation of harmful bacteria due to the antimicrobial and bactericidal activity of the silver.

In the antimicrobial moist wound dressing 10 of the present invention, the external protective film layer 17 is disposed outside the medium layer 13, and acts to prevent wound exudate (secretions) absorbed in the medium layer 13 from being released to the outside environment and dried, thereby maintaining a moist environment. Further, the external protective film layer 17 prevents infiltration of water, bacteria and impurities from the outside environment.

Suitable materials for the external protective film layer 17 include those used commonly in the art, and are preferably polyurethane, polyethylene, polypropylene, polyvinyl chloride, and the like. These materials can prevent infiltration of bacteria and impurities, e.g., water from the outside environment. In addition, since the external protective film layer 17 lets air in, it can allow the skin to breathe. Furthermore, since the external protective film layer 17 is highly expandable and contractible, the wound dressing 10 of the present invention can be suitably used at joint regions.

The external protective film layer 17 is larger in size than the medium layer 13, and the pressure-sensitive adhesive layer 15 can be formed by applying a pressure-sensitive adhesive to surfaces in contact with skin. The pressure-sensitive adhesive layer 15 thus formed is attached to the external protective film layer 17 and acts to firmly fix the external protective film layer 17 to the skin so as to prevent the wound dressing 10 from being separated from the skin.

Any adhesive can be used to form the pressure-sensitive adhesive layer 15 so long as it is commonly used in the art and does not cause any irritation to the skin.

Figure 2:
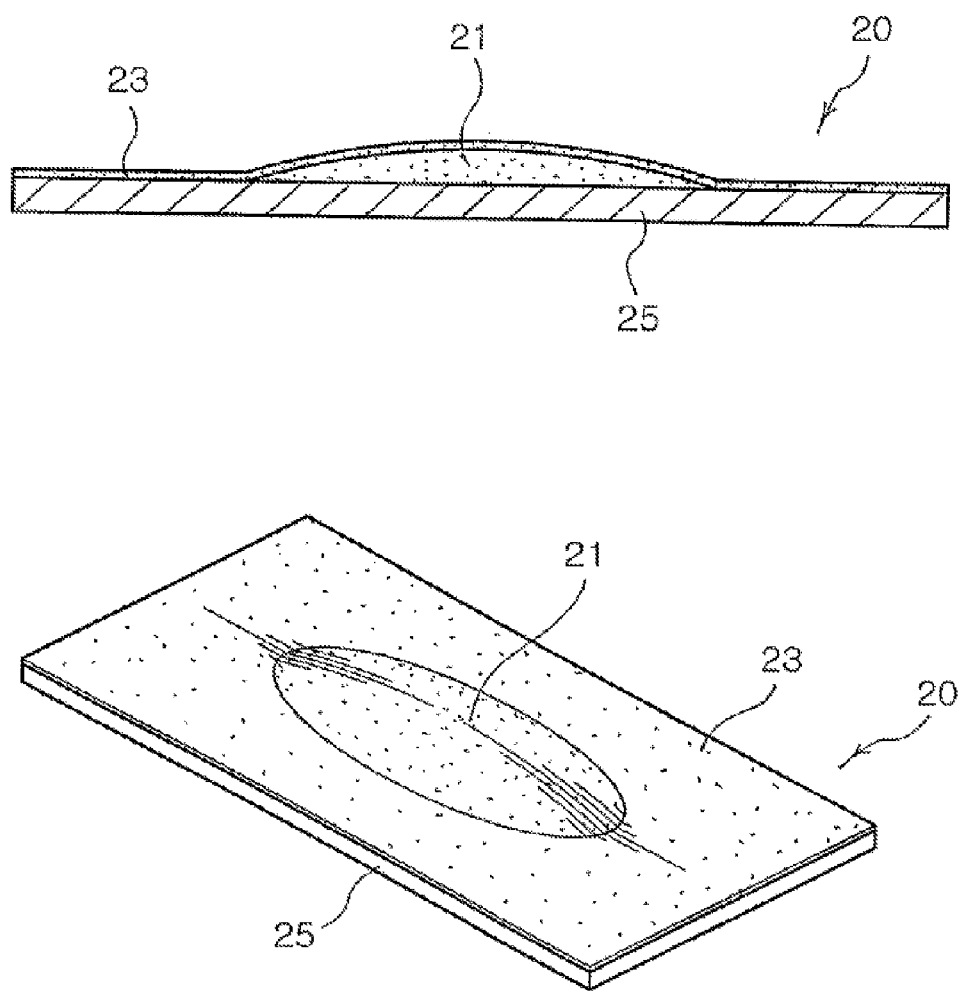
FIG. 2 schematically shows an antimicrobial moist wound dressing comprising a layer in which a silver-CMC powder exists in a hydrogel type, according to another embodiment of the present invention.

An antimicrobial moist wound dressing 20 according to another embodiment of the present invention is shown in FIG. 2. As shown in FIG. 2, the antimicrobial moist wound dressing 20 comprises a pressure-sensitive adhesive layer 23, a silver-CMC powder-containing layer 21, and an external protective film layer 25.

The silver-CMC powder-containing layer 21 is formed by drying a solution of a silver-CMC compound, pulverizing the dried silver-CMC compound to form a powder, followed by hydrogelling. The silver-CMC powder-containing layer 21 is disposed on the external protective film layer 25 and the pressure-sensitive adhesive layer 23 is positioned thereon. The silver-CMC powder-containing layer 21 can absorb moisture of ten or more times of its weight. As a result, the moist wound dressing 20 of the present invention absorbs wound exudate to provide a moist environment. Since the moist wound dressing 20 of the present invention maintains a moist environment, it generates no pain during its removal for exchange and prevents skin tissues from being peeled off from the wound, leaving no scar behind. In addition, the presence of silver bonded to the moist wound dressing allows to inhibit proliferation of harmful bacteria in wound sites.

The external protective film layer 25 serves to prevent release of moisture absorbed in the silver-CMC powder-containing layer 21 to the outside and drying the moisture in ambient air so that the moist wound dressing 20 maintains a moist environment to achieve an environment effective for wound healing. A material for the external protective film layer 25 may be the same as that for the external protective film layer 17. An adhesive for the formation of the pressure-sensitive adhesive layer 23 may be the same as that for the formation of the pressure-sensitive adhesive layer 15.

MODE FOR THE INVENTION

Examples

The present invention will now be described in more detail with reference to the following examples. However, these examples are not intended to limit the present invention.

Preparative Examples 1 to 8

AgCl was dissolved in 25 ml of ammonia water to dissociate silver ions. At this time, the concentrations of the silver-containing compound were adjusted to 0.00001% (w/v), 0.001% (w/v), 0.1% (w/v), 0.5% (w/v), 1% (w/v), 2% (w/v), 3% (w/v) and 6.0% (w/v) (Preparative Examples 1 to 8, respectively), and the concentrations of the ammonium hydroxide were adjusted to 0.1%, 1.0%, 5.0%, 10.0%, 15.0%, 20.0%, 25.0% and 30% (Preparative Examples 1 to 8, respectively). 0.1 g, 0.2 g, 0.3 g, 0.5 g, 1.0 g, 2.5 g, 5.0 g and 10.0 g of solid CMC (Preparative Examples 1 to 8, respectively) were weighed and dissolved in 5 ml of ethanol to prepare solutions.

Each of the silver ion-containing solutions was mixed and reacted with each of the CMC solutions to produce silver-CMC compounds. Each of the silver-CMC compounds was poured into a pure cotton non-woven fabric sheet (size: 10 cm×10 cm, weight: 180 g, thickness: 1 mm) to absorb the compound in the sheet, and dried in hot air at about 95° C. to produce antimicrobial moist wound dressings in which silver in the form of silver oxide was bonded to CMC.

Example 1

Figure 3:
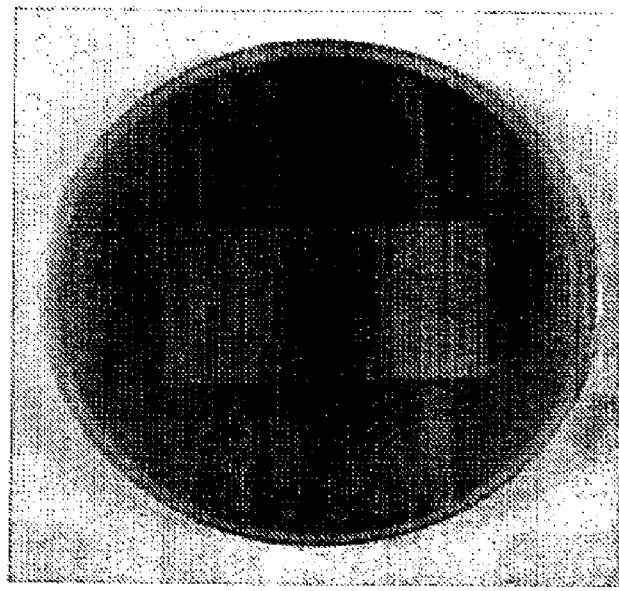
FIGS. 3a and 3b are photographs showing the test results for the antimicrobial activity of an antimicrobial moist wound dressing produced in Preparative Example 4 of the present invention.
Figure 3:
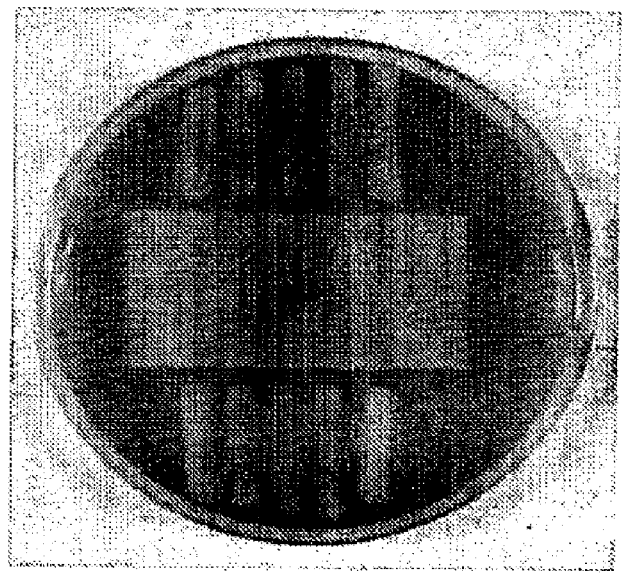

To evaluate the antimicrobial activity of the antimicrobial moist wound dressing produced in Preparative Example 4, a test for the antimicrobial activity was conducted on the antimicrobial moist wound dressing by the AATCC 147-1998 test method (HALO test) in the Korea FITI Testing & Research Institute. As the test strains, *Staphylococcus aureus* (ATCC 6538) and *Kiepsiella pneumoniae* (ATCC 4352) were used. The test results for the antimicrobial activity of the antimicrobial moist wound dressing are shown in FIGS. 3a and 3b. As can be seen from the photographs of FIGS. 3a and 3b, no proliferation of the bacteria was observed at the back surface of the test samples, which demonstrates that the wound dressing of the present invention has superior antimicrobial activity.

Example 2

Analysis for the measurement of silver contents in the antimicrobial moist wound dressing produced in Preparative Example 4 and commercially available wound dressings was requested to the Korea FITI Testing & Research Institute. After the samples were degraded using an acid, the silver contents of the samples were analyzed using an inductively coupled plasma-optical emission spectrometer (ICP-OES). The analytical results are shown in Table 1.

TABLE 1

| Product | Silver Content (mg/kg) |
|---|---|
| Acticoat | 56650.0 |
| Aquacel Ag | 751.0 |
| The product of the present invention (0.5% w/v) | 84.1 |

The results of Table 1 confirm that the silver content of the wound dressing according to the present invention is lowest. Consequently, since the wound dressing of the present invention containing a silver-CMC compound has a lower silver content than the commercially available wound dressings, silver is less dissolved from the wound dressing and thus cells necessary for wound healing are protected against indiscriminate attack by dissolution of silver.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

INDUSTRIAL APPLICABILITY

As apparent from the above description, since silver is chemically bonded to CMC in the antimicrobial moist wound dressings of the present invention, cells necessary for wound healing are protected against attack by dissolution of silver. In addition, since the antimicrobial moist wound dressings of the present invention provide a moist environment effective for wound healing due to superior absorption capacity of CMC, wounds are treated, leaving no scar on the wounds. Furthermore, the moist wound dressings generate no pain during their removal for exchange and provide advantageous effects, including inhibitory effects on the proliferation of bacteria on wounds, due to the presence of silver.

What is claimed is the following:

1. A silver-bonded antimicrobial moist wound dressing comprising:

a pressure-sensitive adhesive layer configured to contact skin, an intermediate layer in which a silver-carboxymethylcellulose (silver-CMC) compound is dispersed in a medium, and an external protective film layer, laminated and bonded to each other, wherein the silver-CMC compound has a CMC-OAg structure of Formula (I):

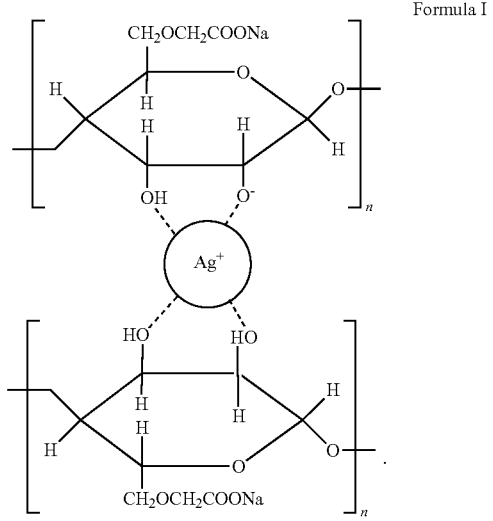

Formula I

2. The wound dressing according to claim 1, wherein the silver-CMC compound is formed by a method comprising the steps of:
adding silver chloride (AgCl) to a 0.1-30% $NH_4OH$ aqueous solution to dissociate silver ions from the silver chloride and form a silver ion-containing solution, wherein the silver chloride is added in an amount of 0.00001% to 20.0% (w/v);
dissolving sodium carboxymethylcellulose in water or an organic solvent to obtain a CMC solution, wherein a concentration of the CMC solution ranges between 2% and 15% (w/v);
mixing the silver ion-containing solution with the CMC solution, and maintaining the mixed solutions at a temperature of 20° C. to 50° C. for 10 seconds to 1 hour so that the hydrogen ions ($H^+$) of the hydroxyl groups of the CMC are replaced by the silver ions to prepare the silver-CMC compound, wherein an amount of the CMC ranges between 0.005 g/ml and 0.035 g/ml of the silver ion-containing solution;
dispersing and absorbing the silver-CMC compound in a medium; and
drying the medium.

3. The wound dressing according to claim 2, wherein the organic solvent is ethanol, isopropyl alcohol or a mixture thereof.

4. The wound dressing according to claim 2, wherein the drying is performed at room temperature to 200° C.

5. The wound dressing according to claim 1, wherein the medium is a pure (100%) cotton non-woven fabric or gauze.

6. The wound dressing according to claim 1, wherein the external protective film layer is larger in size than the intermediate layer, and the pressure-sensitive adhesive layer is formed by applying a pressure-sensitive adhesive to a surface in contact with skin.

7. A silver-bonded antimicrobial moist wound dressing comprising:
a pressure-sensitive adhesive layer in contact with skin;
a silver-carboxymethylcellulose (silver-CMC) powder-containing layer; and
an external protective film layer laminated and bonded to each other,
wherein the silver-CMC powder comprises a silver-CMC compound having a CMC-OAg structure of Formula (I):

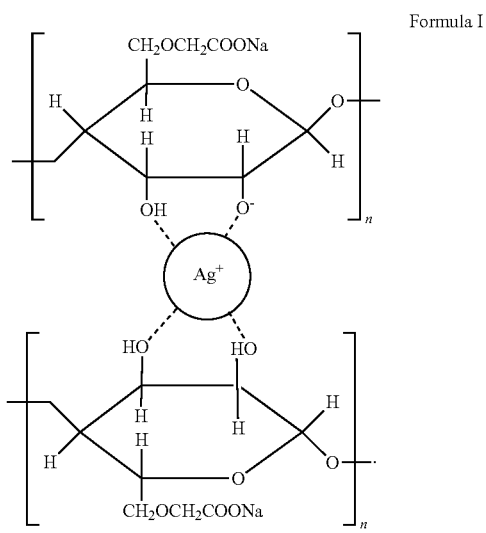

Formula I

8. The wound dressing according to claim 7, wherein the silver-CMC compound is formed by a method comprising the steps of:
adding silver chloride (AgCl) to a 0.1-30% $NH_4OH$ aqueous solution to dissociate silver ions from the silver chloride and form a silver ion-containing solution, wherein the silver chloride is added in an amount of 0.00001% to 20.0% (w/v);
dissolving sodium carboxymethylcellulose in water or an organic solvent to obtain a CMC solution, wherein a concentration of the CMC solution ranges between 2% and 15% (w/v);
mixing the silver ion-containing solution with the CMC solution, and maintaining the mixed solutions at a temperature of 20° C. to 50° C. for 10 seconds to 1 hour so that the hydrogen ions ($H^+$) of the hydroxyl groups of the CMC are replaced by the silver ions to prepare the silver-CMC compound, wherein an amount of the CMC ranges between 0.005 g/ml and 0.035 g/ml of the silver ion-containing solution; and
drying and pulverizing the silver-CMC compound.

9. The wound dressing according to claim 8, wherein the organic solvent is ethanol, isopropyl alcohol or a mixture thereof.

10. The wound dressing according to claim 8, wherein the drying is performed at room temperature to 200° C.

11. The wound dressing according to claim 7, wherein the silver-CMC powder-containing layer is a hydrogel or hydropolymer type.

* * * * *